(12) United States Patent
Tada et al.

(10) Patent No.: US 8,183,283 B2
(45) Date of Patent: May 22, 2012

(54) DENDRITE ELONGATION INHIBITOR FOR MELANOCYTE AND SKIN PREPARATION FOR EXTERNAL USE CONTAINING THE SAME

(75) Inventors: Akihiro Tada, Yokohama (JP); Akiko Kanamaru, Yokohama (JP); Yuko Saeki, Yokohama (JP)

(73) Assignee: Pola Chemical Industries Inc., Shizuoka-shi, Shizuoka (JP)

( * ) Notice: Subject to any disclaimer, the term of this patent is extended or adjusted under 35 U.S.C. 154(b) by 1150 days.

(21) Appl. No.: 10/537,320

(22) PCT Filed: Nov. 28, 2003

(86) PCT No.: PCT/JP03/15267
§ 371 (c)(1),
(2), (4) Date: Jun. 2, 2005

(87) PCT Pub. No.: WO2004/050054
PCT Pub. Date: Jun. 17, 2004

(65) Prior Publication Data
US 2006/0147398 A1    Jul. 6, 2006

(30) Foreign Application Priority Data
Dec. 3, 2002    (JP) .................................. 2002-350733

(51) Int. Cl.
A01N 43/16    (2006.01)
A61K 31/355    (2006.01)
A61K 8/00    (2006.01)
A61K 8/18    (2006.01)
A61Q 5/00    (2006.01)
A61Q 19/02    (2006.01)

(52) U.S. Cl. .......................................... 514/456; 424/62
(58) Field of Classification Search .................. 514/456; 424/62
See application file for complete search history.

(56) References Cited

U.S. PATENT DOCUMENTS
4,935,450 A    6/1990 Cone, Jr.
2002/0065300 A1    5/2002 Seiberg et al.

FOREIGN PATENT DOCUMENTS
EP    0 332 478    9/1989
EP    1147764 A2    10/2001
JP    55-111411    8/1980
JP    02-172907    7/1990
JP    07-017848    1/1995
JP    08-104646    4/1996
JP    10-287544 A1    10/1998
JP    11-246336    9/1999
JP    11-246339    9/1999
JP    11-246347    9/1999
JP    11-349435    12/1999
JP    2001-199866    7/2001
JP    2002-154920    5/2002
WO    WO 02/41909    * 5/2002

OTHER PUBLICATIONS

Flamini, et al. "A Flavonoid Sulphate and Other Compounds from the Roots of *Centaurea bracteata*," *Phytochemistry*, vol. 58, pp. 1229-1233, 2001.
International Search Report, mailed Mar. 16, 2004.
Supplementary European Search Report issued to a corresponding European patent application, dated Jan. 28, 2009.
Office action dated Aug. 11, 2009, issued to related Japanese patent application #2004-556862 with English translation.

* cited by examiner

*Primary Examiner* — Marcos Sznaidman
(74) *Attorney, Agent, or Firm* — Knobbe, Martens, Olson & Bear, LLP

(57) ABSTRACT

The present invention relates to a dendrite elongation inhibitor for melanocytes consisting of a compound represented by the following general formula (1):

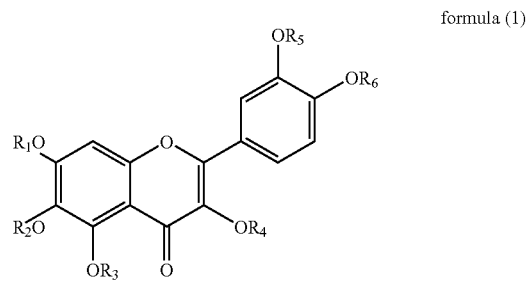

formula (1)

and/or a salt thereof,
wherein $R_1$, $R_2$, $R_3$, $R_4$, $R_5$, and $R_6$ each independently represent a hydrogen atom or a $C_{1-4}$ alkyl group,
and a skin preparation for external use comprising the dendrite elongation inhibitor for melanocytes as an active ingredient.

6 Claims, No Drawings

DENDRITE ELONGATION INHIBITOR FOR MELANOCYTE AND SKIN PREPARATION FOR EXTERNAL USE CONTAINING THE SAME

RELATED APPLICATIONS

This application is the U.S. National Phase under 35 U.S.C. §371 of International Application PCT/JP2003/015267, filed Nov. 28, 2003, which was published in a language other than English and which claims priority of JP Application No. 2002-350733, filed Dec. 3, 2002.

TECHNICAL FIELD

The present invention relates to a dendrite elongation inhibitor for melanocytes and a skin preparation for external use containing the dendrite elongation inhibitor for melanocytes as an active ingredient.

BACKGROUND ART

Many women hope to keep skin fair and beautiful, and many whitening cosmetics have therefore been developed. Examples include whitening cosmetics which contain ascorbic acid or a derivative thereof, kojic acid or a derivative thereof, tranexamic acid or a derivative thereof, hydroquinone glycoside, or the like. However, most of these cosmetics have a mechanism of action in which tyrosinase and thereby biosynthesis of melanin are inhibited with limited effectiveness. That is, even though the whitening cosmetics containing these active ingredients are effective for symptoms such as age spots, freckles, and dark complexion that result from the abnormally accelerated production of melanin, such whitening cosmetics do not have much effect on dyschromatosis for which the amount of melanin produced is a lesser contributing factor. In other words, for dyschromatosis, tyrosinase inhibitors are less effective or not effective at all, and development of means for alleviating such dyschromatosis is desirable.

Examples of dyschromatosis in which melanin production is a lesser contributing factor include dyschromatosis resulting from the accelerated migration of melanin granules from melanocytic dendrites. Although it is considered that such dyschromatosis is treatable by inhibiting the elongation of dendrites that occurs when melanocytes allow melanin granules to migrate, few whitening agents utilizing such a mechanism have been known. There has been a demand for the development of whitening agents utilizing such a mechanism.

The inventors of the present invention have found that *Achillea millefolium* L. is a source plant for Centaureidin (5,7-dihydroxy-3,6-dimethoxy-2-(5-hydroxy-4-methoxyphenyl)-4H-1-benzopyran-4-on; hereinafter also referred to as "Compound I") which is a compound represented by general formula (I). It was known that its extract is useful as a humectant for cosmetics (JP-A 02-172907), and in the stabilization of kojic acid in cosmetics (JP-A 07-17848). The extract inhibits tyrosinase (JP-A 08-104646), eradicates active oxygen (JP-A 11-246336), inhibits α-MSH (JP-A 11-349435), and so on. However, it was not known at all that Centaureidin inhibits the elongation of melanocytic dendrites and that it is useful for alleviating, by such action, dyschromatosis, a condition for which melanin production inhibitors with a tyrosinase inhibitory action are not completely effective.

Moreover, a compound represented by general formula (I), such as Centaureidin, was known:
1) to be found in plants of the genus *Artemisia* and useful for treating allergic diseases (published international application WO 20020419109);
2) to have anti-cancer action (U.S. Pat. No. 493,540); and
3) to be found in plants of the genus *Centaurea cyanus* (Flamini Guido et. al., Phytochemistry, 58 (8), 1229-1233, 2001).

However, it was not known at all that such a substance is present in *Achillea millefolium* L. of the family Asteraceaeis. It was not known in the least that this substance inhibits the elongation of melanocytic dendrites, and that it is useful for alleviating, by such action, dyschromatosis for which melanin production inhibitors with tyrosinase inhibitory action are not completely effective.

DISCLOSURE OF THE INVENTION

The present invention has been achieved under such circumstances, and an object of the present invention is to provide a useful ingredient for inhibiting the elongation of melanocytic dendrites and alleviating, by this action, dyschromatosis refractory to treatment with melanin production inhibitors with tyrosinase inhibitory action.

In light of such circumstances, the inventors have conducted extensive studies and redoubled efforts to acquire a useful ingredient for inhibiting the elongation of melanocytic dendrites and alleviating, by this action, dyschromatosis refractory to treatment with melanin production inhibitors with tyrosinase inhibitory action. As a result, the inventors have completed the present invention by finding that a compound represented by general formula (I) and/or a salt thereof, which can be isolated from *Achillea millefolium* L. of the family Asteraceaeis has such action. Namely, the present invention relates to a technique shown below.

(1) A dendrite elongation inhibitor for melanocytes consisting of a compound represented by the following general formula (1):

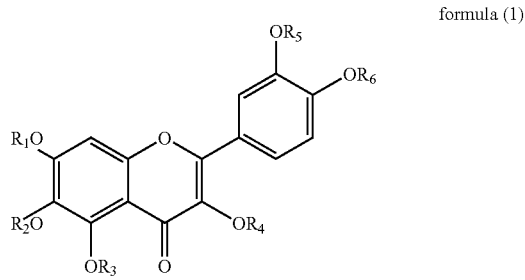

formula (1)

and/or a salt thereof,
wherein $R_1$, $R_2$, $R_3$, $R_4$, $R_5$, and $R_6$ each independently represent a hydrogen atom or a $C_{1-4}$ alkyl group.

(2) The dendrite elongation inhibitor for melanocytes according to (1), characterized in that the compound represented by general formula (1) is Centaureidin indicated by the following formula.

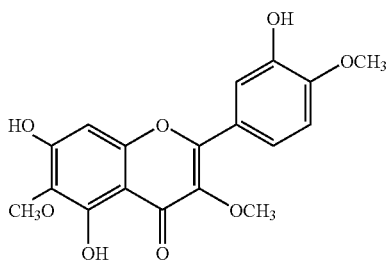

(3) A skin preparation for external use for inhibiting elongation of melanocytic dendrites, comprising the dendrite elongation inhibitor for melanocytes according to (1) or (2) as an active ingredient.

(4) The skin preparation for external use for inhibiting elongation of melanocytic dendrites according to (3), characterized in that the skin preparation for external use is used for alleviating dyschromatosis on which tyrosinase inhibitors have insufficient effect.

(5) The skin preparation for external use for inhibiting elongation of melanocytic dendrites according to (3) or (4), characterized in that the skin preparation for external use is a cosmetic.

BEST MODE FOR CARRYING OUT THE INVENTION (1) Dendrite Elongation Inhibitor for Melanocyte of the Present Invention A dendrite elongation inhibitor for melanocytes of the present invention consists of a compound represented by the above-described general formula (I) and/or a salt thereof.

In general formula (I), $R_1$, $R_2$, $R_3$, $R_4$, $R_5$, and $R_6$ each independently represent a hydrogen atom or an alkyl group.

The alkyl group is preferably a $C_{1-4}$ alkyl group, and examples thereof include a methyl group, an ethyl group, a propyl group, a 1-methylethyl group, a n-butyl group, a 1-methylpropyl group, a 2-methylpropyl group, and a 1,1-dimethylethyl group. Of those, particularly preferred is a methyl group.

The compound represented by general formula (I) can preferably be exemplified by Centaureidin.

Such a compound represented by general formula (I) can be directly used, or can be used in a salt form after treatment with alkali.

The salt can be applied without particular limitation as long as it is physiologically acceptable, and can preferably be exemplified by alkali metal salts such as sodium salts and potassium salts, alkaline-earth metal salts such as calcium salts and magnesium salts, ammonium salts, organic amine salts such as triethanolamine salts, and triethylamine salts, and basic amino acid salts such as lysine salts and arginine salts. Particularly preferred are alkali metal salts, which are easily prepared.

In a skin preparation for external use of the present invention, the compound represented by general formula (I) and/or the salt thereof can be incorporated alone or as a combination of two or more.

Such a compound represented by general formula (I) and/or a salt thereof may be purified, and may be an extract from a plant or a fraction thereof, or the like containing an effective amount of the compound represented by general formula (I) and/or the salt thereof.

Plants of the genus *Achillea* sp. of the family Asteraceaeis, preferably *Achillea millefolium* L. of the family Asteraceaeis can be used to obtain the extract or a fraction thereof. Material used in the extraction of the compound represented by general formula (I) and/or the salt thereof may be the entire plant, a part of the plant containing the compound represented by general formula (I) and/or the salt thereof, or a processed product of the plant. For example, an extract of the above-ground part of the genus *Achillea millefolium* L. of the family Asteraceaeis can be purified and fractionated to obtain the compound represented by general formula (1) and/or the salt thereof. The compound represented by general formula (1) and/or the salt thereof can be identified by X-ray analysis or the like.

The extract is preferably obtained using a highly polar solvent. The highly polar solvent is preferably: ethers such as diethyl ether, isopropyl ether, and tetrahydrofuran; halogenated hydrocarbons such as methylene chloride and chloroform; esters such as ethyl acetate and methyl formate; ketones such as acetone and methylethylketone; nitriles such as acetonitrile; alcohols such as 1,3-butanediol, ethanol, and isopropyl alcohol; and water. Of those, alcohols are particularly preferred. It is noted that the above-described solvent may be one kind or a mixture of two or more.

Extraction may typically be carried out by adding 1 to 10 times by weight of the solvent with respect to the entire plant or a part of the plant, followed by immersion for a few days if carried out at room temperature or a few hours if carried out around the boiling point of the solvent. After extraction, the solvent can be removed by vacuum concentration or the like, if necessary. The compound represented by general formula (I) can be isolated from the extract from which solvent has been removed, by liquid-liquid extraction with ethyl acetate and water, and the like, or purification by silica gel column chromatography using, for example, chloroform-methanol as an eluting solvent, or the like.

A preferable concentration of the compound represented by general formula (I) and/or the salt thereof in a skin preparation for external use of the present invention is 0.001 to 10% by weight, more preferably 0.005 to 5% by weight with respect to the total amount of the skin preparation for external use. This is because, if the concentration is too low, inhibitory action on the elongation of melanocytic dendrites may not be exhibited; while, if the content is too high, the action may level off and may unnecessarily inhibit the degree of freedom of a prescription.

(Example of Production)

Ten kilograms of dried product of the above-ground part of the genus *Achillea millefolium* L. of the family Asteraceaeis was cut into narrow pieces, which were then added to ethanol 50 liter and heated to reflux for 3 hours. After cooling to room temperature, the resulting mixture was concentrated under vacuum concentration, and 1 liter of ethyl acetate and water were added thereto. The resulting mixture was subjected to liquid-liquid extraction to remove ethyl acetate, followed by vacuum concentration to prepare an extract. After dissolving the concentrate in chloroform, the residue was charged on silica gel column chromatography and purified with an eluting solvent chloroform:methanol=100:1 to 70:30 to give 211.5 mg of Compound 1. The structure was determined by X-ray analysis.

(2) Skin Preparation for External Use of the Present Invention

A skin preparation for external use of the present invention is characterized by containing the above-described dendrite elongation inhibitor for melanocytes. As used herein, a skin preparation for external use is a general term for compositions applied externally to skin, and can be exemplified by cosmetics including quasi-drugs, dermatologic drugs for external use, and dermatologic sundry articles for external use. Of those, particularly preferred are cosmetics. This is because the above-described melanocyte dendrite elongation inhibitor of the present invention has excellent safety, so that the melanocyte dendrite elongation inhibitor can be used continually and habitually as a cosmetic, and more satisfactorily exhibit whitening action with such a usage pattern.

The dosage forms of cosmetics are not particularly limited and the cosmetics can be used not only in emulsified dosage forms such as cream and milky lotions but in solution dosage forms such as skin lotions and essences, because the dendrite elongation inhibitor of the present invention has particularly high physical properties of polarity.

Skin preparation for external use of the present invention can contain optional ingredients used generally in skin preparations for external use, besides the dendrite elongation inhibitor for melanocytes described above. Preferable examples of optional ingredients include: hydrocarbons such as squalene, liquidparaffin, light-gravity liquid isoparaffin, heavy-gravity liquid isoparaffin, microcrystalline wax, and solid paraffin; silicones such as dimethycon, femethycon, cyclomethycon, amodimethycon, polyether denatured silicone; esters such as jojoba oil, carnauba wax, haze wax, bees wax, spermaceti wax, octyldodecyl oleate, isopropyl myristate, neopentyl glycol diisostearate, and malic diisostearate; aliphatic acids such as stearic acid, lauric acid, myristic acid, palmitic acid, isostearic acid, isopalmitic acid, behenic acid, and oleic acid; higher alcohols such as behenyl alcohol (1-docosanol), cetanol, oleyl alcohol, and octadecyl alcohol; triglycerides such as castor oil, coconut oil, hydrofined coconut oil, camellia oil, wheat germ oil, isostearate triglyceride, isooctanoate triglyceride, and olive oil; polyhydric alcohols such as 1,3-butanediol, glycerin, diglycerin, dipropylene glycol, polyethylene glycol, 1,2-pentandiol, 1,2-hexylene glycol, and isoprene glycol; nonionic detergents such as sorbitan sesquiolate, sorbitan monooleate, sorbitan trioleate, sorbitan sesquistearate, sorbitanmonostearate, polyoxyethylene sorbitan monooleate, polyoxyethylene sorbitan monostearate, polyoxyethylene stearate, polyoxyethyleneoleate, polyoxyethylene glyceril fatty ester, polyexyethylene alkyl ether, and polyoxyethylene hardened castor oil; anionic detergents such as sodium lauryl stearate, polyoxyethylene alkyl sulfate, and sulfosuccinate; cationic detergents such as quaternary alkyl ammonium salt; ampholytic detergents such as alkyl betaine; organic powders such as crystalline cellulose, crosslinking type methylpolysiloxane, polyethylene powder, and acrylic resin powder; powders that can be surface-treated such as talc, mica, sericite, magnesium carbonate, calcium carbonate, titaniumdioxide, iron oxide, iron blue, ultramarine, titanic mica, titanic sericite, and silica; thickening agents such as alkyl acrylate-alkyl methacrylate copolymer and/or a salt thereof, carboxyvinyl polymer and/or a salt thereof, xanthan gum, and hydroxypropyl cellulose; active ingredients such as vitamins, terpenes, and steroids; examples of vitamins include retinol, retinoic acid, tocopherol, riboflavin, pyridoxin, ascorbic acid, and ascorbic phosphate; examples of terpenes include glycyrrhizic acid salt, glycyrrhetin, ursolic acid, and oleanolic acid; examples of steroids include estradiol, ethynilestradiol, and estriol; antiseptic agents such as phenoxyethanol, parabens, Hibitane Gluconate, and benzalkonium chloride; and UV absorbing agents such as dimethylamino benzoate, cinnamates, and benzophenones.

Of course, a whitening agent having a different mechanism from that of the dendrite elongation inhibitor of the present invention, for example, ascorbic acid or a derivative thereof, kojic acid or a derivative thereof, tranexamic acid or a derivative thereof, hydroquinone glycoside, or the like, can also be incorporated in the skin preparation for external use. Incorporating such a whitening agent gives at least a synergistic effect and is therefore preferred. A preferable content of such a whitening agent having a different mechanism from that of the dendrite elongation inhibitor of the present invention is 0.01 to 5% by weight in total with respect to the total amount of the skin preparation for external use.

The skin preparation for external use of the present invention is preferably applicable for treatment of dyschromatosis on which tyrosinase inhibitors have insufficient effects. "Dyschromatosis on which tyrosinase inhibitors have insufficient effects" used herein means dyschromatosis judged by 70% or more panelists to be "dyschromatosis having no alleviation" when tested by a method described in Example 2 or the like using a tyrosinase inhibitor (e.g., arbutin).

The skin preparation for external use of the present invention can be produced by combining the above-described essential ingredient and an optional ingredient according to a standard method.

EXAMPLES

Although the present invention will more fully be described hereinafter with reference to Examples, it is understood that the present invention is not intended to be limited only to such Examples.

Example 1

According to a method shown below, inhibitory action on the elongation of dendrites was examined using human melanocytes. (Reagent, etc.) Cells, basal media, and amplification additives were purchased from KURABO INDUSTRIES LTD.
(Cell) Normal human melanocyte
(Medium) Basal medium (Medium 1545) supplemented with reagents described below
(Reagent) Amplification additive: bovine pituitary extract (BPE) (final concentration of 0.4% v/v in the medium), fetal bovine serum (FBS) (final concentration of 0.5% v/v in the medium), human recombinant basic fibroblast growth factor (rFGF-B) (final concentration of 3 ng/ml in the medium), hydrocortisone (final concentration of 0.18 µg/ml in the medium), insulin (final concentration 5 µg/ml in the medium), transferrin (final concentration of 5 µg/ml in the medium), phorbol 12-myristate 13-acetate (PMA) (final concentration of 10 ng/ml in the medium), heparin (final concentration of 3 µg/ml in the medium), and PSA solution (mixture solution of penicillin concentration of 50,000 Unit/ml, streptomycin concentration of 50 µg/ml, and amphotericin B concentration of 12.5 µg/ml; 1-ml addition with respect to 500 ml of the medium)
(Method)
The extract of *Achillea millefolium* L. and Compound 1 (Centaureidin) obtained in the above-described example of production were diluted in a basal medium so that the concentration of Centaureidin was brought up to 100 µg/ml, to make a sample solution. It is noted that a control is a solution having only basal medium.

Normal human melanocytes were inoculated into a 48-well microplate (3,000 cells/well, 200 µl medium) and cultured at 37° C.

After 24 hours, 50 µl of the sample solution was added thereto.

Inhibition against the elongation of dendrites was observed 24 hours after addition of the sample solution.

(Result)

The result is shown in Table 1 by the length of the dendrite. It is seen that the dendrite is elongated in the control by the effect of adding the growth factor, while elongation is inhibited in the Centaureidin group.

TABLE 1

| Added compound | Length of dendrite(μm) |
|---|---|
| Centaureidin | 26 ± 8 |
| Extract of *Achillea millefolium* L. | 108 ± 21 |
| Control | 140 ± 29 |

Example 2

According to a prescription shown below, a cosmetic that was a skin preparation for external use of the present invention was prepared. That is, ingredients of I, II, and III each were heated to 70° C. II was neutralized with III and emulsified by gradually adding I with stirring. The resulting mixture was homogenized with a homogenizer, followed by cooling with stirring to give a milky lotion. Comparative Example 1 in which Compound 1 in this prescription was substituted by squalene was prepared. Twenty persons in total (10 persons for each group) suffering from dark complexion that was not alleviated by usual cosmetics for inhibiting the production of melanin were used to examine the degree of alleviation of dark complexion with use at twice per day, in the morning and evening for 30 consecutive days. The degree of alleviation was evaluated after 30-day use by the following scoring system: Score 5: significantly alleviated, Score 4: obviously alleviated, Score 3: alleviated, Score 2: slightly alleviated, and Score 1: not alleviated. The result is shown in Table 2. The result shows that the cosmetic that is the skin preparation for external use of the present invention has excellent whitening effect.

| I | |
|---|---|
| Squalene | 10 parts by weight |
| Sorbitan sesquistearate | 2 parts by weight |
| Compound 1 | 0.05 part by weight |
| Butylparaben | 0.1 part by weight |
| II | |
| 1,3-buthanediol | 5 parts by weight |
| Xanthan gum | 0.1 part by weight |
| Acrylate alkyl-methacrylate alkyl (C10–30) | 0.4 part by weight |
| Methylparaben | 0.1 part by weight |
| Water | 50 parts by weight |
| III | |
| Potassium hydroxide | 0.2 part by weight |
| Water | 32.05 parts by weight |

TABLE 2

| Sample | Score 5 | Score 4 | Score 3 | Score 2 | Score 1 |
|---|---|---|---|---|---|
| Example 2 | | 4 | 4 | 2 | |
| Comparative Example 1 | | | | 2 | 8 |

Example 3

A skin preparation for external use (cosmetic) was made in the same way as in Example 2 except that the amount of Compound 1 was changed, and similarly evaluated using 10 similar panelists. Similar effect was observed in this skin preparation for external use.

| I | |
|---|---|
| Squalene | 10 parts by weight |
| Sorbitan sesquistearate | 2 parts by weight |
| Compound 1 | 0.1 part by weight |
| Butylparaben | 0.1 part by weight |
| II | |
| 1,3-buthanediol | 5 parts by weight |
| Xanthan gum | 0.1 part by weight |
| Acrylate alkyl-methacrylate alkyl (C10–30) | 0.4 part by weight |
| Methylparaben | 0.1 part by weight |
| Water | 50 parts by weight |
| III | |
| Potassium hydroxide | 0.2 part by weight |
| Water | 32.0 parts by weight |

TABLE 3

| Sample | Score 5 | Score 4 | Score 3 | Score 2 | Score 1 |
|---|---|---|---|---|---|
| Example 3 | | 5 | 4 | 1 | |

Example 4

According to a prescription shown below, a skin preparation for external use (cosmetic) was made in the same way as in Examples and 3, and similarly evaluated using similar panelists. Comparative Example 2 in which Compound 1 was substituted by arbutin was made and similarly evaluated. The results are shown in Table 4. This result shows that less whitening effect due to the tyrosinase inhibitor was observed in the panelists and that the dendrite elongation inhibitor for melanocytes of the present invention was observed to effectively act even in such panelists.

| I | |
|---|---|
| Squalene | 10 parts by weight |
| Sorbitan sesquistearate | 2 parts by weight |
| Compound 1 | 1 part by weight |
| Butylparaben | 0.1 part by weight |
| II | |
| 1,3-buthanediol | 5 parts by weight |
| Xanthan gum | 0.1 part by weight |
| Acrylate alkyl-methacrylate alkyl (C10–30) | 0.4 part by Weight |
| Methylparaben | 0.1 part by weight |
| Water | 50 parts by weight |
| III | |
| Potassium hydroxide | 0.2 part by weight |
| Water | 31.1 parts by weight |

TABLE 4

| Sample | Score 5 | Score 4 | Score 3 | Score 2 | Score 1 |
|---|---|---|---|---|---|
| Example 4 | 1 | 6 | 3 | | |
| Comparative Example 2 | | | | 3 | 7 |

INDUSTRIAL APPLICABILITY

According to the present invention, a useful ingredient for inhibiting the elongation of melanocytic dendrites and alleviating, by this action, dyschromatosis which is refractive to melanin production inhibitors utilizing a tyrosinase inhibitory action is provided.

What is claimed is:

1. A method for whitening skin comprising:
a step of applying Centaureidin represented by the following formula and/or a salt thereof to the skin of an individual in need of skin whitening, whereby elongation of melanocytic dendrites is inhibited:

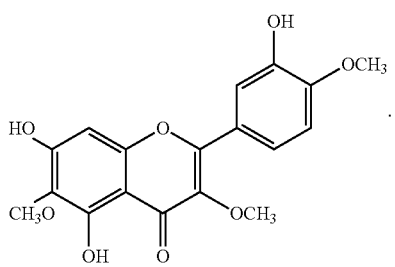

2. A method for whitening skin comprising applying a skin preparation for external use comprising 0.005 to 5% by weight of Centaureidin represented by the following formula and/or a salt thereof to an individual in need of skin whitening, whereby elongation of melanocytic dendrites is inhibited:

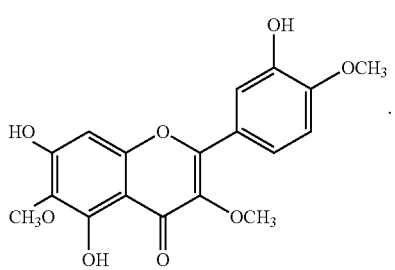

3. The method for whitening skin according to claim 2, wherein the skin preparation for external use is a cosmetic.

4. A method for treating dyschromatosis comprising:
a step of applying Centaureidin represented by the following formula and/or a salt thereof to the skin of an individual in need of a treatment for dyschromatosis, whereby elongation of melanocytic dendrites is inhibited:

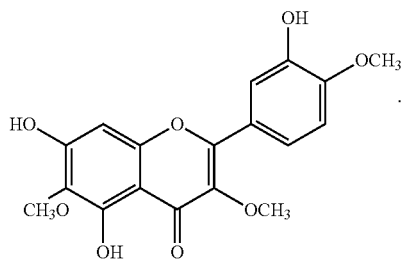

5. A method for treating dyschromatosis comprising applying a skin preparation for external use comprising 0.005 to 5% by weight of Centaureidin represented by the following formula and/or a salt thereof to an individual in need of a treatment for dyschromatosis, whereby elongation of melanocytic dendrites is inhibited:

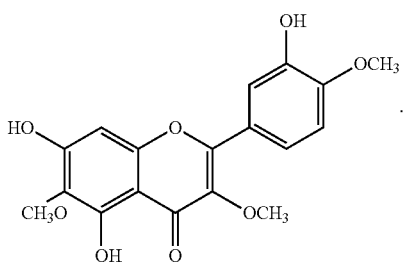

6. The method for treating dyschromatosis according to claim 5, wherein the skin preparation for external use is a cosmetic.

* * * * *

UNITED STATES PATENT AND TRADEMARK OFFICE
CERTIFICATE OF CORRECTION

PATENT NO.         : 8,183,283 B2
APPLICATION NO.    : 10/537320
DATED              : May 22, 2012
INVENTOR(S)        : Tada et al.

It is certified that error appears in the above-identified patent and that said Letters Patent is hereby corrected as shown below:

Column 1, Line 58, "as "Compound I")" should be changed to --as "Compound 1")--

Column 1, Line 59, "formula (I)." should be changed to --formula (1).--

Column 2, Line 4, "formula (I)," should be changed to --formula (1),--

Column 2, Line 40, "general formula (I)" should be changed to --general formula (1)--

Column 3, Line 34, "general formula (I)" should be changed to --general formula (1)--

Column 3, Line 35, "general formula (I)," should be changed to --general formula (1),--

Column 3, Line 43, "general formula (I)" should be changed to --general formula (1)--

Column 3, Line 45, "general formula (I)" should be changed to --general formula (1)--

Column 3, Line 58, "general formula (I)" should be changed to --general formula (1)--

Column 3, Line 61, "general formula (I)" should be changed to --general formula (1)--

Column 3, Line 64, "general formula (I)" should be changed to --general formula (1)--

Column 4, Line 3, "formula (I)" should be changed to --formula (1)--

Column 4, Line 5, "general formula (I)" should be changed to --general formula (1)--

Column 4, Line 30, "(I) can be" should be changed to --(1) can be--

Column 4, Line 36, "general formula (I)" should be changed to --general formula (1)--

Column 5, Line 20, "such as dimethycon," should be changed to --such as dimethicone,--

Column 5, Line 21, "cyclomethycon, amodimethycon," should be changed to
    --cyclomethycone, amodimethycone,--

Column 5, Line 35, "sorbitan sesquiolate," should be changed to --sorbitan sesquioleate,--

Column 5, Line 39, "glyceril fatty" should be changed to --glyceryl fatty--

Column 5, Lines 39-40, "polyexyethylene alkyl" should be changed to --polyoxyethylene alkyl--

Column 5, Line 58, "ethynilestradiol, and" should be changed to --ethinylestradiol, and--

Column 6, Line 37, "(Medium 1545)" should be changed to --(Medium 154S)--

Signed and Sealed this
Twentieth Day of November, 2012

David J. Kappos
*Director of the United States Patent and Trademark Office*

CERTIFICATE OF CORRECTION (continued)
U.S. Pat. No. 8,183,283 B2

Column 7, Line 46, "1,3-buthanediol" should be changed to --1,3-butanediol--

Column 8, Line 13, "1,3-buthanediol" should be changed to --1,3-butanediol--

Column 8, Line 34, "Examples and 3," should be changed to --Examples 2 and 3,--

Column 8, Line 51, "1,3-buthanediol" should be changed to --1,3-butanediol--